United States Patent [19]

Biggs et al.

[11] Patent Number: 4,907,458
[45] Date of Patent: Mar. 13, 1990

[54] PULL TESTING

[76] Inventors: Kenneth L. Biggs, 3407 N. Valley View, Orange, Calif. 92667; C. Fredrick Miller, 1551 E. Pacifico, Anaheim, Calif. 92805

[21] Appl. No.: 130,308

[22] Filed: Dec. 9, 1987

[51] Int. Cl.⁴ .............................................. G01N 3/08
[52] U.S. Cl. .................................. 73/827; 73/862.42
[58] Field of Search ..................... 73/827, 862.42, 842, 73/826

[56] References Cited

U.S. PATENT DOCUMENTS 3,564,911  2/1971  Stemmons et al. ............... 73/827 X
3,580,065  5/1971  Strittmater et al. ............... ⊖/827 X Primary Examiner—Jerry W. Myracle

[57] ABSTRACT

An apparatus and method for conducting pull testing of the wires and wire bonds of an electronic apparatus in which a bond wire is engaged by a hook, and the force with which that wire is urged to move away from the hook is measured as the force required to maintain the hook stationary.

9 Claims, 1 Drawing Sheet

PULL TESTING

This invention relates to methods and apparatus by which to test the strength with which connecting wires are bonded to their respective circuit points in electronic microcircuitry.

BACKGROUND

Large numbers of electronic components can be formed and interconnected as integrated circuitry on a common substrate or "chip" without the need for separate wire interconnections. However, wires are used extensively to connect integrated circuit chips to non-integrated circuit components and to other integrated circuits and to connector leads and pins.

Interconnection is accomplished by bonding one end of a wire to a first circuit point with the aid of a bonding tool. A length of wire is paid out to form a loop of wire from that first circuit point to a second circuit point. The wire is bonded to that second circuit point and the standing part of the wire is broken adjacent to the second circuit point. In most cases the bonding is accomplished by placing the end of a bonding tool against the upper surface of the wire and applying pressure to hold the lower surface of the wire against the circuit point to which the wire is to be bonded. Sonic energy is imparted to the wire and the circuit point at the end of the bonding tool in a degree which causes mechanical and electrical bonding of the wire and circuit point. There are alternative ways to accomplish the bond. One of those methods utilizes an adhesive filled with electrically conductive material to join the wire and the circuit point electrically and mechanically.

Whatever the bonding technique, in certain cases it is desireable to test to determine whether the bond has sufficient strength to withstand forces which it might be subjected in use. In a nondestructive test the wire is pulled in the direction away from the circuit point using a degree of force greater than any force that might be expected when the circuitry is placed in service. If the wire does not break, the wire and its bonds are considered fit for placement in service. When the cost of a bond failure is sufficiently high, when it might mean loss of life or loss of a multimillion dollar satellite, for example, every bond is tested. In other cases such, for example, as when the sonic bonding apparatus is being adjusted, it may be desireable to discover what pulling force will cause the wire or a bond to break. In others it may be desireable to pull on the wire and discover the amount of the force at which it yields.

To pull on a wire with some specified amount of force is not a complex concept. To accomplish it has proven to be very difficult. The wires used in connecting circuit points in microcircuitry are usually made of gold or aluminum. The diameter of the wire may be as much as 1.5 mills or one half the thickness of an ordinary human hair to as little as 0.7 mills or one fourth the diameter of a human hair. The circuit points to which the wires are bonded may have a surface area not much larger than the cross sectional area of a human hair. The length of the wire that extends between two bond points is often no more than a few hundredths of a centimeter. A high powered, stereo microscope is used to view such wires and circuit points and bonds. That presents two kinds of problems. The physical size of the material to be tested and the test apparatus are very tiny and the forces involved are almost minuscule. A typical pull force to be used in testing such bonds is less than the weight of a feather and may be in the order of the difference in the weight of feathers. A pull force of only 0.5 grams and testing of every bond is commonly specified in tests of electronic apparatus destined for military and space applications. Given the size, mass and the inertial forces that are developed in apparatus capable of holding a microcircuit unit while grasping and pulling the wires and measuring the pull force to conduct such test was thought to be impossible and it may be impossible in practice. This invention provides a method and apparatus which has made such testing possible.

SUMMARY OF THE INVENTION

It is a object of the invention to provide a practical method and apparatus by which microcircuitry wire bonds may be tested.

Another object is to provide such a method and apparatus which will provide accurate measurements in a reasonably short time with minimum operator fatigue.

A further object is to provide a method and apparatus by which such testing may be accomplished wit a high degree of accuracy whether the test be to pull with a specified force or to measure yield point or breaking point of the wire.

A still further object is to provide an apparatus by which positioning of the hook and wire in preparation for the test can be accomplished by manipulation of a single lever.

These and other objects and advantages of the invention which will become apparent on examination of the accompanying drawings and of the following specification are realized in part by the method of:

placing a hook under the wire;

maintaining the position of the hook substantially fixed;

pulling said bond point away from said position while measuring the magnitude of the pulling force applied to the hook.

In the preferred method the hook is fixed to a structure whose vertical position remains substantially fixed while the magnitude of the pulling force is measured. Further, it is preferred that the vertical position of the electronic apparatus remain fixed while the hook is moved vertically and rotationally to place the hook under a wire notwithstanding that such a method requires capability of vertical movement of both the electronic apparatus and the hook.

The invention may be practiced by an apparatus which is characterized as apparatus in which a bond wire is engaged by a hook and the force with which that wire is urged to move away from the hook is measured as the force required to maintain the hook stationary.

IN THE DRAWINGS

FIG. 1 is a perspective drawing of a pull testing machine shown schematically; and FIG. 2 is schematic drawing of preferred apparatus according to the invention by which to practice the preferred method of the invention.

DESCRIPTION OF THE PREFERRED EMBODIMENT

Figure 1:
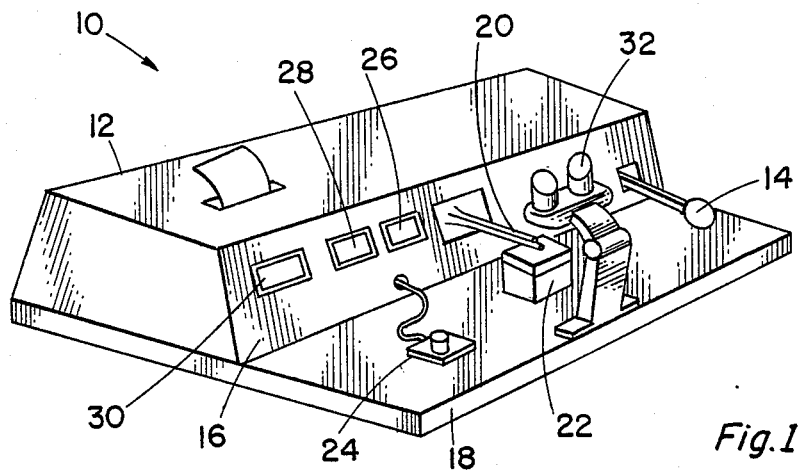

The pull testing machine 10 of FIG. 1 includes a cabinet 12 in which a micromanipulator, electronic control and display circuitry and a printer are housed. A manipulator control arm 14 extends through the front panel 16 at the right of the unit over a work table or apron 18. A hook arm 20 extends through the panel at its mid-region so that its end is positioned above a work platform 22. The platform rests on apron 18. Its upper surface can be raised and lowered to lift and lower an electronic apparatus to be tested. The numeral 24 identifies a manual control unit which, in this model, is portable and is connected by a cable the electronic circuitry in the cabinet 12. Several display units are mounted such as to be visible on the panel 16. One of them indicates pull force, it is numbered 26. Another, 28, indicates the rate at which the platform is to be lowered and another, 30, indicates the maximum pull force which the machine will exert on a test piece.

In operation, the apparatus whose wire bonds are to be tested is secured to the upper, work surface of the platform 22. Using the control arm 14, with the aid of the stereo microscope 32, an operator moves the hook arm 20 to position a miniature hook adjacent to, and below a wire whose bonds are to be tested. The hook is rotated by manipulation of the manual control unit 24 so that the hook underlies the wire. The operator then signals the start of the test by operation of the manual control 24. The platform lowers the test piece and the wire to be pulled while the hook remains stationary, The wire pulls on the hook and the hook arm. The force of that pull is measured and is displayed at display 26. When the force of the pull reaches a predefined value in the nondestructive test mode, platform movement is stopped. After a time delay the platform is raised and the hook is rotated ninety degrees. If the printer has been activated a record of the test is printed on a tape a portion of which is visible at 34 in FIG. 1. If the wire is broken or a bond gives way, the display and the printer will record the maximum pull force. The control circuitry can be set to continue to pull until there is breakage.

In the preferred method, the weight of the hook, hook arm and the weight of any hook arm operating structure that has the effect of urging the hook downwardly is supported on a scale such that any increase in force on the hook is a measure of the pull on the wire and bonds to be tested. It is preferred that motion of the wire and its bonds be vertical and that the pull force be vertical but that is not essential. Also, it is preferred that all forces other than pull force be nulled out to the end that the display and the printer display and record only pull force.

Figure 2:
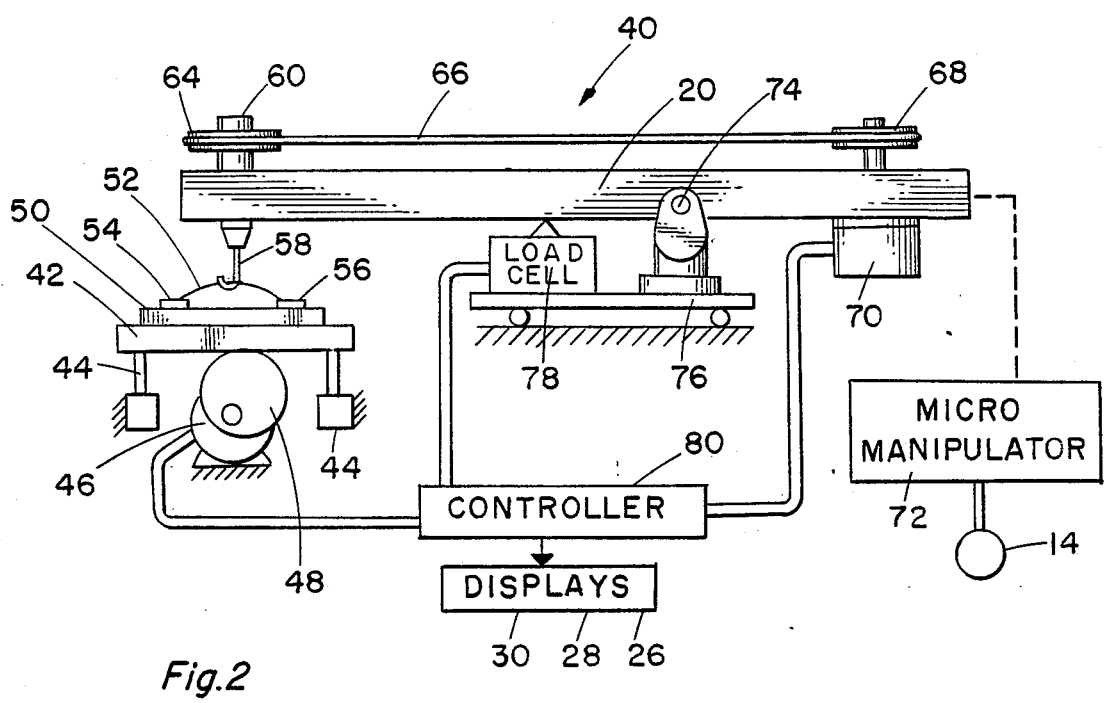

A schematic diagram of the entire system 40 is shown in FIG. 2. The platform 22 of is represented as comprising a plate 42 which is mounted on guides 44 to indicate that it can be raised and lowered in response to rotation of stepping motor 48. In FIG. two the table is lowered by gravity as permitted by rotation of cam 46 and it forced upward by action of the cam. Alternatively the motor can be used to lower the plate using a screw drive or other arrangement. The work piece 50 whose wires and bonds are to be tested is mounted atop the plate 42. A wire 52 to be tested along with the bonds 54 and 56 at its ends are shown very much enlarged for the sake of clarity. So too is the hook 58. The hook extends downwardly from a spindle 60 which is journaled for rotation about an axis substantially perpendicular to horizontal beam 62. At the upper side of the beam the spindle carries a pulley 64. An endless belt 66 extends around pulley 64 at the outer end of the beam and a second pulley 68 at the inner end of the beam. Pulley 68 is fixed to the rotatable shaft of a hook rotating stepping motor 70 which motor is fixed to the beam 62. The ground symbols represent the frame of the machine.

The invention may be practiced by maintaining the hook stationary and moving the work piece 50 to position the wire to be pulled under the hook with or without movement of the plate 42. Alternatively, the work piece is maintained stationary and the beam 62 is moved to position the hook over the wire to be tested. Another alternative would be to combine positioning of both work piece and the beam. The preferred course is to keep the position of the work piece fixed and move the hook by moving the beam and to move the beam with the micromanipulator described in U.S. Pat. No. 3,474,685 granted 28 Oct. 1969 to C. F. Miller. Such a manipulator is represented by the micromanipulator block 72. The manipulator is connected to move the hook arm 20, comprising the assembly of beam 62, pulleys 64 and 68, belt 66, motor 70 and spindle 60. It moves the hook arm in the x, y and z directions in response to movements of the manipulator control arm 14. To represent that, the beam 62 is shown to be mounted on a horizontal pivot 74 for beam movement in the vertical plane. The pivot is mounted for rotation in the horizontal plane on a turn table 76 and the turntable can be moved back and forth in the horizontal plane. In this preferred embodiment pull force is measured in a standard load cell 78 of high sensitivity even at extremely light loads. The cell is positioned such that the force exerted on it by the hook arm, micromanipulator 72 or any other structure either is constant or varies in negligible amount relative to pull force during the conduct of a pull test. That could be accomplished by fixed mounting of the cell relative to apron 18 or ground which represents the machine's frame. The lever arm from pivot 74 to the load cell would change in that arrangement. Suitable compensation could be provided in the computation of pull force. It is possible to eliminate that compensation requirement by mounting the load cell on the turntable 76. The micromanipulator makes that conveniently possible. In this configuration the beam 62 is made to rest on the load cell when the hook is in position below the wire to be pulled before the wire is pulled. Other, equivalent arrangements may be employed. The force on the load cell is determined so that it can be nulled out prior to making the pull test or can be subtracted from the sum of the pretest force plus the test force. The preferred load cell supplies an electrical output utilizing, for example, the piezoelectric effect. While they require some physical displacement to provide a measurement of force, the amount of displacement is very small so that the position of the cell during measurement is fixed or substantially so.

The preferred controller 80 utilizes a microprocessor programmed, in whatever language the programmer is familiar with or prefers, to perform the functions herein described. The several displays respond to digital signals. Motors 48 and 70 are stepping motors which are powered by pulses. The analog output of the load cell is change to a digital signal of high resolution. The printer responds to digital signals. In the preferred embodiment, stepping motor is made to simulate the smooth, analog rotation of a direct current motor by digital shaping of its energizing pulses. Motor speed is controlled be controlling pulse rate. Pull force values are placed in memory for comparison with stored standards in the case of non-destructive testing or for identification of break or yield force. All of those functions are within the power of ordinary computers and the skill of programmers to provide within the ordinary exercise of their skill.

In the preferred arrangement, the wire pulls the hook rather than the hook pulling the wire. Notwithstanding that it requires provision for independent vertical movement of both hook and the apparatus to be tested, that arrangement greatly reduces the number of variables, mostly forces, which can operate to alter the measured value of force.

In accordance with the rules, the best mode now known for practicing the invention has been shown in the accompanying drawing and described in the specification above. However, it is to be understood that other embodiments and variations of the invention are possible and that the invention is to be limited by what is defined in the appended claims rather than by what has been shown.

We claim:

1. The method of testing the ability of a wire bond between a wire and a bond point to withstand being pulled, which method comprises the steps of:
   placing a hook under the wire;
   maintaining the position of the hook substantially fixed;
   pulling said bond point away from said position while measuring the magnitude of the pulling force applied to the hook.

2. The method of conducting pull testing of the wires and wire bonds of a electronic apparatus, which method comprises the steps of:
   fixing said electronic apparatus at a horizontal position below a hook such that the wires and bonds of said apparatus are exposed above said position;
   altering the horizontal position of one of the hook and the apparatus and altering the vertical position and rotational orientation of the hook to place the hook under a wire of said apparatus;
   utilizing said wire to pull the hook by lowering the electronic apparatus; and
   maintaining the vertical position of the hook substantially fixed while measuring the magnitude of the force with which the wire pulls on the hook.

3. The method of conducting pull testing of the wires and wire bonds of a electronic apparatus, which method comprises the steps of:
   fixing said electronic apparatus at a horizontal position below a hook such that the wires and bonds of said apparatus are exposed above said position;
   altering the horizontal position of one of the hook and the apparatus and altering the vertical position and rotational orientation of the hook to place the hook under a wire of said apparatus;
   utilizing said wire to pull the hook by lowering the electronic apparatus; and
   measuring the magnitude of the force with which the wire pulls on the hook
   the step of measuring the magnitude with which the wire pulls on the hook is accomplished by fixing said hook to a structure which bears on a force measuring structure whose vertical position remains fixed during the measurement.

4. The method defined in claim 3 in which the step of utilizing the wire to pull the hook by lowering the electronic apparatus is continued until the magnitude of the force with which the wire pulls on the hook reaches a predefined magnitude.

5. The invention defined in claim 4 which comprises the subsequent step of raising the electronic apparatus until the wire is raised above the kook in a degree sufficient to permit rotation of the hook such that it does not underlie the wire.

6. A structure for conducting pull testing of wires and wire bonds of an electronic apparatus, which structure comprises:
   a frame;
   a hook;
   means for maintaining the position of said hook constant relative to said frame in a given direction;
   means for urging motion of an electronic apparatus in said given direction away from said hook while a wire of the electronic apparatus is engaged by the hook; and
   means for measuring the force with which the hook resists such motion of said electronic apparatus.

7. A structure for conducting pull testing of wire s and wire bonds of an electronic apparatus, which structure comprises:
   a frame;
   a hook; means for maintaining the position of said hook constant relative to said frame in a given direction;
   means for urging motion of an electronic apparatus in said given direction away from said hook while a wire of the electronic apparatus is engaged by the hook;
   means for measuring the force with which the hook resists such motion of said electronic apparatus; and
   a movable platform to which an electronic apparatus can be fixed and moved to alter it's position in said direction; and
   a hook rotator capable of rotating said hook about an axis which extends substantially in said direction.

8. The invention defined in claim 7 which further comprises manipulator means for altering the vertical and horizontal position of said hook and said means for measuring the force.

9. The invention defined in claim 8 in which said manipulator means comprises a single lever micromanipulator.

* * * * *